US010500235B2

(12) United States Patent
Wardell

(10) Patent No.: US 10,500,235 B2
(45) Date of Patent: Dec. 10, 2019

(54) WOUND HEALING COMPOSITIONS COMPRISING BUCKWHEAT HONEY AND METHYLGLYOXAL AND METHODS OF USE

(71) Applicant: SanMelix Laboratories, Inc., Hollywood, FL (US)

(72) Inventor: Mark R. Wardell, Fort Myers, FL (US)

(73) Assignee: San Melix Laboratories, Inc., Pembroke Pines, FL (US)

(*) Notice: Subject to any disclaimer, the term of this patent is extended or adjusted under 35 U.S.C. 154(b) by 0 days.

(21) Appl. No.: 15/010,896

(22) Filed: Jan. 29, 2016

(65) Prior Publication Data

US 2016/0220722 A1  Aug. 4, 2016

Related U.S. Application Data

(60) Provisional application No. 62/109,369, filed on Jan. 29, 2015.

(51) Int. Cl.
*A61K 35/644* (2015.01)
*A61K 33/06* (2006.01)
*A61K 33/00* (2006.01)
*A61K 33/30* (2006.01)
*A61K 33/04* (2006.01)
*A61L 15/40* (2006.01)
*A61K 31/121* (2006.01)
*A61K 9/00* (2006.01)
*A61L 15/46* (2006.01)
*A61L 26/00* (2006.01)
*A61K 31/11* (2006.01)
*A61L 15/20* (2006.01)

(52) U.S. Cl.
CPC .......... *A61K 35/644* (2013.01); *A61K 9/0014* (2013.01); *A61K 31/11* (2013.01); *A61K 31/121* (2013.01); *A61K 33/00* (2013.01); *A61K 33/04* (2013.01); *A61K 33/06* (2013.01); *A61K 33/30* (2013.01); *A61L 15/20* (2013.01); *A61L 15/40* (2013.01); *A61L 15/46* (2013.01); *A61L 26/0057* (2013.01); *A61L 26/0066* (2013.01); *A61L 2300/102* (2013.01); *A61L 2300/216* (2013.01); *A61L 2300/30* (2013.01); *A61L 2300/404* (2013.01)

(58) Field of Classification Search
CPC .... A61K 9/0014; A61K 31/11; A61K 31/121; A61K 33/00; A61K 33/06; A61K 33/04; A61K 33/30; A61K 35/644; A61L 15/20; A61L 15/46; A61L 26/0057; A61L 26/0066; A61L 2300/102; A61L 2300/216; A61L 2300/30; A61L 2300/404

See application file for complete search history.

(56) References Cited

U.S. PATENT DOCUMENTS

| 4,401,651 | A | 8/1983 | Knutson |
| 5,080,900 | A | 1/1992 | Stanley |
| 5,089,606 | A | 2/1992 | Cole |
| 5,407,670 | A | 4/1995 | Shinault |
| 5,652,274 | A | 7/1997 | Martin |
| 5,980,875 | A | 11/1999 | Mousa |
| 6,149,947 | A | 11/2000 | Hon et al. |
| 6,956,144 | B2 | 10/2005 | Molan |
| 7,014,870 | B1 | 3/2006 | Hon et al. |
| 2004/0127826 | A1 | 7/2004 | Caskey |
| 2005/0033213 | A1 | 2/2005 | Bray et al. |
| 2008/0249485 | A1 | 10/2008 | Effing |
| 2008/0292715 | A1 | 11/2008 | Snow et al. |
| 2009/0304780 | A1* | 12/2009 | van den Berg ...... A61K 35/644 424/447 |
| 2011/0104279 | A1 | 5/2011 | Marraccini et al. |
| 2011/0171284 | A1 | 7/2011 | Gilman |
| 2012/0269879 | A1* | 10/2012 | Watson ................. A61L 15/40 424/445 |
| 2014/0194803 | A1 | 7/2014 | Parks et al. |
| 2016/0022730 | A1 | 1/2016 | Baker et al. |
| 2016/0346335 | A1 | 12/2016 | Alvarado |

FOREIGN PATENT DOCUMENTS

NZ  2005/120250  12/2005
WO  WO 2005/120250 A1  12/2005

OTHER PUBLICATIONS

Jervis-Brady et al., Methylglyoxal-Infused Honey Mimics the Anti-*Staphylococcus aureus* Biofilm Activity of Manuka Honey: Potential Implication in Chronic Rhinosinusitis, May 2011, Laryngoscope, v. 121, pp. 1104-1107.*
Torreya, Wound Care Product Opportunity, Apr. 2012, pp. 1-4.*
Molan, "The evidence and the rationale for the use of honey as wound dressing", Dec. 2011, Wound Practice and Research, vol. 19 iss. 4, pp. 204-220.*
Torreya, Wound Care Product Opportunity Executive Summary, Apr. 2012, First Texas Medical Partners, LLC, pp. 1-4.*
Efem, Clinical observations on the wound healing properties of honer, Jul. 1998, British Journal of Surgery, vol. 75, pp. 679-681.*
Ranzato et al., Honey Exposure Stimulates Wound Repair of Human Dermal Fibroblasts, Jun. 2013, Burns & Trauma, vol. 1 iss. 1, pp. 32-38.*
Fidaleo et al., Methylglyoxal: A New Weapon Against Staphylococcal Wound Infections, Feb. 27, 2010, Chem. Lett., vol. 39, pp. 322-323.*
Majtan et al., Anti-biofilm Effects of Honey Against Wound Pathogens Proteus mirabilis and Enterobacter cloacae, Mar. 11, 2013, Phytotherapy Research, vol. 28, pp. 69-75.*

(Continued)

*Primary Examiner* — Ali Soroush
(74) *Attorney, Agent, or Firm* — Trueba & Suarez PLLC; Darlene Barron

(57) ABSTRACT

The invention provides compositions based on medicinal honey containing broad-spectrum antibacterial activities of peroxide, polyphenols and methylglyoxal, for the treatment of wounds; and methods of treating a wound, comprising contacting a wound with the above composition or a wound dressing containing the above composition.

4 Claims, 4 Drawing Sheets

(56) References Cited

OTHER PUBLICATIONS

Sarkar U, Lopez A, Maselli JH, Gonzales R. Adverse drug events in U.S. adult ambulatory medical care. *Health services research.* Oct. 2011, 46(5): 1517-1533.
Lazarou J, Pomeranz BH, Corey PN. Incidence of adverse drug reactions in hospitalized patients: a meta-analysis of prospective studies. *JAMA.* Apr. 15, 1998, 279(15): 1200-1205.
Mwitari PG, Ayeka PA, Ondicho J, Matu EN, Bii CC. Antimicrobial activity and probable mechanisms of action of medicinal plants of Kenya: Withania somnifera, Warbugia ugandensis, Prunus africana and Plectrunthus barbatus. *PLoS One.* 2013, 8(6): e65619.
Bent S. Herbal medicine in the United States: review of efficacy, safety, and regulation: grand rounds at University of California, San Francisco Medical Center. *Journal of general internal medicine.* Jun. 2008, 23(6): 854-859.
Domitrovic R, Potocnjak I. A comprehensive overview of hepatoprotective natural compounds: mechanism of action and clinical perspectives. *Archives of toxicology.* Jan. 2016, 90(1): 39-79.
Kuropatnicki AK, Szliszka E, Krol W. Historical aspects of propolis research in modern times. *Evid Based Complement Alternat Med.* 2013, 2013: 964149.
Herbology—Herbalism. Crystalinks. Available from: http://www.crystalinks.com/herbology.html. Accessed Apr. 26, 2016.
Cowan MM. Plant products as antimicrobial agents. *Clinical microbiology reviews.* 1999, 12(4): 564-582.
Ablin JN, Hauser W, Buskila D. Spa treatment (balneotherapy) for fibromyalgia-a qualitative-narrative review and a historical perspective. *Evid Based Complement Alternat Med.* 2013, 2013: 638050.
Bogdanov S. Nature and origin of the antibacterial substances in honey. *Lebensm-Wiss u-Technol.* 1997, 30: 748-753.
Adcock D. The effect of catalase on the inhibine and peroxide values of various honeys. *Journal of Apicultural Research.* 1962, 1: 38-40.
White JW, Jr., Subers MH, Schepartz Al. The identification of inhibine, the antibacterial factor in honey, as hydrogen peroxide and its origin in a honey glucose-oxidase system. *Biochimica et biophysica acta.* May 7, 1963, 73: 57-70.
Brudzynski K. Effect of hydrogen peroxide on antibacterial activities of Canadian honeys. *Canadian journal of microbiology.* Dec. 2006, 52(12): 1228-1237.
Molan P. The antibacterial activity of honey. 1. The nature of the antibacterial activity. *Bee World.* 1992, 73(1): 5-28.
Molan PC. Honey as a topical antibacterial agent for treatment of infected wounds. *World Wide Wounds.* 2001. Available from: http://www.worldwidewounds.com/2001/november/Molan/honey-as-topical-agent.html. Accessed Apr. 26, 2016.
Russell KM, Molan PC, Wilkins AL, Holland PT. Identification of some antibacterial constituents of New Zealand manuka honey. *Journal of Agricultural and Food Chemistry.* 1990, 38(1): 10-13.
Mavric E, Wittmann S, Barth G, Henle T. Identification and quantification of methylglyoxal as the dominant antibacterial constituent of Manuka (*Leptospermum scoparium*) honeys from New Zealand. *Molecular nutrition & food research.* Apr. 2008, 52(4): 483-489.
Adams CJ, Boult CH, Deadman BJ, Farr JM, Grainger MN, Manley-Harris M, Snow MJ. Isolation by HPLC and characterisation of the bioactive fraction of New Zealand manuka (*Leptospermum scoparium*) honey. *Carbohydrate research.* Mar. 17, 2008, 343(4): 651-659.
Adams CJ, Boult CH, Deadman BJ, Farr JM, Grainger MN, Manley-Harris M, Snow MJ. Erratum: Isolation by HPLC and characterisation of the bioactive fraction of New Zealand manuka (*Leptospermum scoparium*) honey. *Carbohydrate research.* Dec. 14, 2009, 344(18): 2609.
Atrott J, Henle T. Methylglyoxal in manuka honey—correlation with antibacterial properties. *Czech J Food Sci.* 2009, 27: S163-S165.
Allen KL, Molan PC, Reid GM. A survey of the antibacterial activity of some New Zealand honeys. *The Journal of pharmacy and pharmacology.* Dec. 1991, 43(12): 817-822.

Adams CJ, Manley-Harris M, Molan PC. The origin of methylglyoxal in New Zealand manuka (*Leptospermum scoparium*) honey. *Carbohydrate research.* May 26, 2009, 344(8): 1050-1053.
Kwakman PH, te Velde AA, de Boer L, Speijer D, Vandenbroucke-Grauls CM, Zaat SA. How honey kills bacteria. *FASEB journal : official publication of the Federation of American Societies for Experimental Biology.* Jul. 2010, 24(7): 2576-2582.
Brudzynski K, Abubaker K, Miotto D. Unraveling a mechanism of honey antibacterial action: Polyphenol/H2O2-induced oxidative effect on bacterial cell growth and on DNA degradation. *Food Chemistry.* 2012, 133: 329-336.
Brudzynski K, Lannigan R. Mechanism of Honey Bacteriostatic Action Against MRSA and VRE Involves Hydroxyl Radicals Generated from Honey's Hydrogen Peroxide. *Frontiers in microbiology.* 2012, 3: 36.
Brudzynski K, Abubaker K, Wang T. Powerful bacterial killing by buckwheat honeys is concentration-dependent, involves complete DNA degradation and requires hydrogen peroxide. *Frontiers in microbiology.* 2012, 3: 242.
Honey—Health and Therapeutic Qualities; Provided by The National Honey Board. Available from: http://www.biologiq.nl/UserFiles/Compendium_Honey_2002.pdf. Accessed Apr. 26, 2016.
Israili ZH. Antimicrobial properties of honey. *American journal of therapeutics.* Jul.-Aug. 2014, 21(4): 304-323.
Frankel S, Robinson GE, Berenbaum MR. Antioxidant capacity and correlated characteristics of 14 unifloral honeys. *Journal of Apicultural Research.* 1998, 37(1): 27-31.
Chen L, Mehta A, Berenbaum M, Zangerl AR, Engeseth NJ. Honeys from different floral sources as inhibitors of enzymatic browning in fruit and vegetable homogenates. *J Agric Food Chem.* Oct. 2000, 48(10): 4997-5000.
van den Berg AJ, van den Worm E, van Ufford HC, Halkes SB, Hoekstra MJ, Beukelman CJ. An in vitro examination of the antioxidant and anti-inflammatory properties of buckwheat honey. *Journal of wound care.* Apr. 2008, 17(4): 172-174, 176-178.
Gheldof N, Wang XH, Engeseth NJ. Buckwheat honey increases serum antioxidant capacity in humans. *J Agric Food Chem.* 2003, 51(5): 1500-1505.
Alvarez-Suarez JM, Giampieri F, Battino M. Honey as a source of dietary antioxidants: structures, bioavailability and evidence of protective effects against human chronic diseases. *Current medicinal chemistry.* 2013, 20(5): 621-638.
Molan PC. Re-introducing honey in the management of wounds and ulcers—theory and practice. *Ostomy/wound management.* Nov. 2002, 48(11): 28-40.
Kwakman PH, Zaat SA. Antibacterial components of honey. *IUBMB life.* Jan. 2012, 64(1): 48-55.
Maddocks SE, Lopez MS, Rowlands RS, Cooper RA. Manuka honey inhibits the development of *Streptococcus pyogenes* biofilms and causes reduced expression of two fibronectin binding proteins. *Microbiology.* Mar. 2012, 158(Pt 3): 781-790.
Nassar HM, Li M, Gregory RL. Effect of honey on *Streptococcus mutans* growth and biofilm formation. *Applied and environmental microbiology.* Jan. 2012, 78(2): 536-540.
Molan P. The antibacterial activity of honey. 2. Variation in the potency of the antibacterial activity. *Bee World.* 1992, 73(2): 59-76.
Molan P. Pdf 6: The antibacterial activity of honey and its role in treating diseases2012 Sep. 26, 2013. Available from: http://www.academia.edu/2189571/Pdf_6_The_antibacterial_activity_of_honey_and_its_role_in_treating_diseases.
Basualdo C, Sgroy V, Finola MS, Marioli JM. Comparison of the antibacterial activity of honey from different provenance against bacteria usually isolated from skin wounds. *Veterinary microbiology.* Oct. 6, 2007, 124(3-4): 375-381.
Molan PC. Debridement of wounds with honey. *Journal of Wound Technology.* 2009, 5: 12-17.
Efem SE. Clinical observations on the wound healing properties of honey. *The British journal of surgery.* Jul. 1988, 75(7): 679-681.
Subrahmanyam M. Honey dressing versus boiled potato peel in the treatment of burns: A prospective randomized study. *Burns : journal of the International Society for Burn Injuries.* Sep. 1996, 22(6): 491-493.

(56) References Cited

OTHER PUBLICATIONS

Subrahmanyam M. A prospective randomised clinical and histological study of superficial burn wound healing with honey and silver sulfadiazine. *Burns : journal of the International Society for Burn Injuries*. Mar. 1998, 24(2): 157-161.

Molan PC. Potential of honey in the treatment of wounds and burns. *American journal of clinical dermatology*. 2001, 2(1): 13-19.

Subrahmanyam M. Topical application of honey for burn wound treatment—an overview. *Ann Burns Fire Disasters*. Sep. 30, 2007, 20(3): 137-139.

Paul IM, Beiler J, McMonagle A, Shaffer ML, Duda L, Berlin CM, Jr. Effect of honey, dextromethorphan, and no treatment on nocturnal cough and sleep quality for coughing children and their parents. *Archives of pediatrics & adolescent medicine*. Dec. 2007, 161(12): 1140-1146.

Boroumand P, Zamani MM, Saeedi M, Rouhbakhshfar O, Hosseini Motlagh SR, Aarabi Moghaddam F. Post tonsillectomy pain: can honey reduce the analgesic requirements? *Anesthesiology and pain medicine*. Summer, 2013, 3(1): 198-202.

Lazim NM, Abdullah B, Salim R. The effect of Tualang honey in enhancing post tonsillectomy healing process. An open labelled prospective clinical trial. *International Journal of Pediatric Otorhinolaryngology*. 2013, 77: 457-461.

Lee DS, Sinno S, Khachemoune A. Honey and wound healing: an overview. *American journal of clinical dermatology*. Jun. 1, 2011, 12(3): 181-190.

Al Somal N, Coley KE, Molan PC, Hancock BM. Susceptibility of Helicobacter pylori to the antibacterial activity of manuka honey. *Journal of the Royal Society of Medicine*. Jan. 1994, 87(1): 9-12.

Othman NH. Honey and cancer: Sustainable inverse relationship particularly for developing nations—a review. *Evidence-Based Complementary and Alternative Medicine*. 2012, 2012: 10 pages.

Ahmed S, Othman NH. Honey as a potential natural anticancer agent: A review of its mechanisms. *Evidence-Based Complementary and Alternative Medicine*. 2013, 2013: 7 pages.

Vit P, Rodriguez-Malaver A, Rondon C, Gonzalez I, Luisa Di Bernardo M, Ysabel Garcia M. Bioactive indicators related to bioelements of eight unifloral honeys. *Archivos latinoamericanos de nutricion*. Dec. 2010, 60(4): 405-410.

Huttunen S, Riihinen K, Kauhanen J, Tikkanen-Kaukanen C. Antimicrobial activity of different Finnish monofloral honeys against human pathogenic bacteria. *APMIS : acta pathologica, microbiologica, et immunologica Scandinavica*. Sep. 2013, 121(9): 827-834.

Mundo MA, Padilla-Zakour OI, Worobo RW. Growth inhibition of foodborne pathogens and food spoilage organisms by select raw honeys. *Int J Food Microbiol*. Dec. 1, 2004, 97(1): 1-8.

Zhou J, Li P, Cheng N, Gao H, Wang B, Wei Y, Cao W. Protective effects of buckwheat honey on DNA damage induced by hydroxyl radicals. *Food Chem Toxicol*. Aug. 2012, 50(8): 2766-2773.

Ohashi K, Natori S, Kubo T. Expression of amylase and glucose oxidase in the hypopharyngeal gland with an age-dependent role change of the worker honeybee (*Apis mellifera* L.). *European journal of biochemistry / FEBS*. Oct. 1, 1999, 265(1): 127-133.

Suwannapong G, Chaiwongwattanakul S, M.E. B. Histochemical comparison of the hypopharyngeal gland in *Apis cerana* Fabricus, 1793 workers and *Apis mellifera* Linnaeus, 1758 workers. *Psyche*. 2010, 2010: 7 pages.

Bucekova M, Valachova I, Kohutova L, Prochazka E, Klaudiny J, Majtan J. Honeybee glucose oxidase—its expression in honeybee workers and comparative analyses of its content and H2O2-mediated antibacterial activity in natural honeys. *Die Naturwissenschaften*. Aug. 2014, 101(8): 661-670.

Li Y, Trush MA. DNA damage resulting from the oxidation of hydroquinone by copper: role for a Cu(II)/Cu(I) redox cycle and reactive oxygen generation. *Carcinogenesis*. Jul. 1993, 14(7): 1303-1311.

Li Y, Trush MA. Reactive oxygen-dependent DNA damage resulting from the oxidation of phenolic compounds by a copper-redox cycle mechanism. *Cancer Res*. Apr. 1, 1994, 54(7 Suppl): 1895s-1898s.

Sakihama Y, Cohen MF, Grace SC, Yamasaki H. Plant phenolic antioxidant and prooxidant activities: phenolics-induced oxidative damage mediated by metals in plants. *Toxicology*. Aug. 1, 2002, 177(1): 67-80.

Fujiwara S, Imai J, Fujiwara M, Yaeshima T, Kawashima T, Kobayashi K. A potent antibacterial protein in royal jelly. Purification and determination of the primary structure of royalisin. *J Biol Chem*. Jul. 5, 1990, 265(19): 11333-11337.

*Herbal Medicine*. University of Maryland Medical Center. Available from: http://umm.edu/health/medical/altmed/treatment/herbal-medicine. Accessed Apr. 27, 2016.

Weindorf M, Korber A, Klode J, Dissemond J. Non-interventional study to investigate the efficacy and safety of Tegaderm Matrix in the treatment of patients with therapy-refractory chronic wounds. *Journal der Deutschen Dermatologischen Gesellschaft—Journal of the German Society of Dermatology : JDDG*. Jun. 2012, 10(6): 412-420.

Katz U, Schoenfeld Y, Zakin V, Sherer Y, Sukenik S. Scientific evidence of the therapeutic effects of dead sea treatments: a systematic review. *Semin Arthritis Rheum*. 2012, 42(2): 186-200.

Matz H, Orion E, Wolf R. Balneotherapy in dermatology. *Dermatologic therapy*. 2003, 16(2): 132-140.

Davis A. Medicines by design. U.S. Department of Health and Human Services; National Institutes of Health; National Institute of General Medical Sciences. NIH Publication No. 06-474. 2006, 28-37 pages. Available from: http://publications.nigms.nih.gov/medbydesign/medbydesign.pdf. Accessed Apr. 27, 2016.

*The Benefits of Dead Sea Salt*. SALTWORKS. America's Sea Salt Company. Available from: http://www.saltworks.us/salt_info/si_DeadSeaSalt_Benefits.asp. Accessed Apr. 27, 2016.

*About the Dead Sea*. SALTWORKS. America's Sea Salt Company. Available from: http://www.saltworks.us/salt_info/si_DeadSeaSalt_Info.asp. Accessed Apr. 27, 2016.

Dead Sea Salts—Technical Data. Available from: http://www.chemistrystore.com/deadseasalts.pdf. Accessed Apr. 27, 2016.

*Dead Sea Salt*. Available from: https://en.wikipedia.org/wiki/Dead_Sea_salt. Accessed Apr. 27, 2016.

*Seawater*. Wikipedia, the Free Encyclopedia. Available from: http://en.wikipedia.org/wiki/Seawater. Accessed May 6, 2016.

*Dead Sea—Chemistry and health effects*. motishemesh7 on ebay. Available from: http://www.ebay.com/gds/Dead-Sea-Chemistry-and-health-effects-/10000000004197733/g.html. Accessed Apr. 27, 2016.

Lippard SJ. *Metals in Medicine*. pp. 505-506. Available from: http://authors.library.caltech.edu/25052/10/BioinCh_chapter9.pdf. Accessed Apr. 27, 2016.

Ma'or Z, Henis Y, Alon Y, Orlov E, Sorensen KB, Oren A. Antimicrobial properties of Dead Sea black mineral mud. *International journal of dermatology*. May 2006, 45(5): 504-511.

Proksch E, Nissen HP, Bremgartner M, Urquhart C. Bathing in a magnesium-rich Dead Sea salt solution improves skin barrier function, enhances skin hydration, and reduces inflammation in atopic dry skin. *International journal of dermatology*. Feb. 2005, 44(2): 151-157.

Schempp CM, Dittmar HC, Hummler D, Simon-Haarhaus B, Schulte-Monting J, Schopf E, Simon JC. Magnesium ions inhibit the antigen-presenting function of human epidermal Langerhans cells in vivo and in vitro. Involvement of ATPase, HLA-DR, B7 molecules, and cytokines. *The Journal of investigative dermatology*. Oct. 2000, 115(4): 680-686.

Bellometti S, Giannini S, Sartori L, Crepaldi G. Cytokine levels in osteoarthrosis patients undergoing mud bath therapy. *International journal of clinical pharmacology research*. 1997, 17(4): 149-153.

Dean C. *The Magnesium Miracle*. 2014 Revised and Updated Edition. The Kindle Edition. Ballantine Books, New York, 2014.

Shani J, Seidl V, Hristakieva E, Stanimirovic A, Burdo A, Harari M. Indications, contraindications and possible side-effects of climatotherapy at the Dead-Sea. *International journal of dermatology*. Jul. 1997, 36(7): 481-492.

Sukenik S, Neumann L, Buskila D, Kleiner-Baumgarten A, Zimlichman S, Horowitz J. Dead Sea bath salts for the treatment of rheumatoid arthritis. *Clinical and experimental rheumatology*. Jul.-Aug. 1990, 8(4): 353-357.

(56) References Cited

OTHER PUBLICATIONS

Sherman G, Zeller L, Avriel A, Friger M, Harari M, Sukenik S. Intermittent balneotherapy at the Dead Sea area for patients with knee osteoarthritis. *The Israel Medical Association journal : IMAJ.* Feb. 2009, 11(2): 88-93.
Cordray S, Harjo JB, Miner L. Comparison of intranasal hypertonic dead sea saline spray and intranasal aqueous triamcinolone spray in seasonal allergic rhinitis. *Ear, nose, & throat journal.* Jul. 2005, 84(7): 426-430.
Depoortere D, Kofonow JM, Chen B, Chiu AG, Cohen NA. Murine Ciliotoxicity and Rabbit Sinus Mucosal Healing by Polyhydrated Ionogen. *Otolaryngology—head and neck surgery : official journal of American Academy of Otolaryngology-Head and Neck Surgery.* 2011, 145(3): 482-488.
DePoortere D, Kofonow JM, Chiu AG, Cohen NA. Polyhydrated ionogen enhances postoperative sinonasal ciliated remucosalization. *International forum of allergy & rhinology.* Mar.-Apr. 2011, 1(2): 83-87.
Kane DP. *Chronic wound healing and chronic wound management.* In: Chronic Wound Care: A Clinical Resource Book for Healthcare Professionals, 4th edition. Krasner D.L., Rodeheaver G.T., Sibbald R.G., (eds.). Malvern, HMP Communications, 2007, pp. 11-24.
Stechmiller J, Schultz G. *Chronic wound healing and chronic wound management.* In: Chronic Wound Care: A Clinical Resource Book for Healthcare Professionals, 4th edition. Krasner D.L., Rodeheaver G.T., Sibbald R.G., (eds.). Malvern, HMP Communications, 2007, pp. 67-73.
Bennett NT, Schultz GS. Growth factors and wound healing: biochemical properties of growth factors and their receptors. *American journal of surgery.* Jun. 1993, 165(6): 728-737.
Nwomeh BC, Yager DR, Cohen IK. Physiology of the chronic wound. *Clinics in plastic surgery.* Jul. 1998, 25(3): 341-356.
Krasner DL, Rodeheaver GT, Sibbald RG. *Chronic Wound Care: A Clinical Resource Book for Healthcare Professionals.* HMP Communications, Malvern, 2007.
Mast BA, Schultz GS. Interactions of cytokines, growth factors, and proteases in acute and chronic wounds. *Wound repair and regeneration : official publication of the Wound Healing Society [and] the European Tissue Repair Society.* Oct. 1996, 4(4): 411-420.
Number of surgeries performed in the U.S. each year. Available from: http://www.cdc.gov/nchs/fastats/inpatient-surgery.htm. Accessed Mar. 20, 2013.
De Guzman JM. Wound dehiscence. Available from: http://j_deguzman_gsj.tripod.com/wound_dehiscence.htm. Accessed Jun. 6, 2016.
*Prevalence and incidence of postoperative abdominal wound dehiscence.* Available from: http://www.rightdiagnosis.com/p/postoperative_abdominal_wound_dehiscence/prevalence.htm. Accessed May 10, 2016.
Desrosiers M, Myntti M, James G. Methods for removing bacterial biofilms: in vitro study using clinical chronic rhinosinusitis specimens. *American journal of rhinology.* Sep.-Oct. 2007, 21(5): 527-532.
Davis A. Medicines by design. U.S. Department of Health and Human Services; National Institutes of Health; National Institute of General Medical Sciences. NIH Publication No. 06-474. 2006, 28-37 pp. Available from: http://publications.nigms.nih.gov/medbydesign/medbydesign.pdf. Accessed Apr. 27, 2016.
White JW, Jr., Subers MH, Schepartz AI. The identification of inhibine, the antibacterial factor in honey, as hydrogen peroxide and its origin in a honey glucose-oxidase system. Biochimica et biophysica acta. May 7, 1963, 73: 57-70.
Brudzynski K, Abubaker K, Mioffo D. Unraveling a mechanism of honey antibacterial action: Polyphenol/H2O2-induced oxidative effect on bacterial cell growth and on DNA degradation. Food Chemistry. 2012, 133: 329-336.
Zumla A. et al., "Honey—a remedy rediscovered," Journal of the Royal Society of Medicine, vol. 82, Jul. 1989, pp. 384-385.
Armon P., "The use of honey in the treatment of infected wounds," Tropical Doctor, 1980, 10, p. 91.
Molan P., "The Evidence Supporting the Use of Honey as a Wound Dressing," Seminar Review, Lower Extremity Wounds 5(1); 2006, pp. 40-54.
Molan P., "Clinical usage of honey as a wound dressing: an update," 2004 J Wound Care 13 (9):353-356.
White, Jr., "Composition of Honey" Chapter 5, 1975 in Crane E(ed) Honey: A comprehensive survey, Heinemann, London, pp. 157-206.
Fernandes Abbade L. et al., "Venous ulcer: epidemiology, physiopathology, diagnosis and treatment," 2004 International Journal of Dermatology 2005, 44, pp. 449-456.
Günes U. et al., "Effectiveness of a Honey Dressing for Healing Pressure Ulcers," J WOCN, Mar./Apr. 2007, p. 184.
Okeniyi J et al. "Comparison of Healing of Incised Abscess Wounds with Honey and EUSOL Dressing" The Journal of Alternative and Complementary Medicine, vol. 11, No. 3, 2005, pp. 511-513.
Subrahmanyam M., "Honey-impregnated gauze versus amniotic membrane in the treatment of burns," Burns (1994) 20, (4) pp. 331-333.
Ndayisaba G. et al., "Clinical and bacteriologic result of wounds treated with honey. An analysis of 40 patients," The Journal of Orthopaedic Surgery, 1993, 7, No. 2—English abstract.
Kramer S., "Effect of povidone-iodine on wound healing: A review," 1999 Journal of Vascular Nursing, vol. XVII, No. 1, p. 17.
Mphande A et al., "Effects of honey and sugar dressings on wound healing," Journal of Wound Care vol. 16, No. 7, Jul. 2007.
Subrahmanyam M., "Topical application of honey in treatment of burns," Br. J. surg. 1991, vol. 78, April, pp. 497-498.
Medhi B. et al., "Topical Application of Honey in the Treatment of Wound Healing: A Metaanalysis," Alternative Medicine vol. 10, No. 4, Oct.-Dec. 2008.
Postmes T. et al., "Honey for wounds, ulcers, and skin graft preservation" The Lancet, vol. 341:Mar. 20, 1993, pp. 756-757.
Ranzato E. et al., "Platelet lysate modulates MMP-2 and MMP-9 expression, matrix deposition and cell-to-matrix adhesion in keratinocytes and fibroblasts," 2010 John Wiley & Sons A/S., Experimental Dermatology, 20, pp. 308-313.
Gurtner G. et al., "Wound repair and regeneration" Insight Review—Nature, vol. 453, May 15, 2008.
Ranzato E. et al., "Epithelial mesenchymal transition traits in honey-driven keratinocyte wound healing: comparison among different honeys," Wound Rep Reg (2012) 20 pp. 778-785.
Ranzato E. et al., Platelet lysate promotes in vitro wound scratch closure of human dermal fibroblasts: different roles of cell calcium, P38, ERK and PI3K/AKT, J. Cell. Mol. Med. vol. 13, No. 8b, 2009, pp. 2030-2038.
Ranzato E. et al., "HMGb1 promotes scratch wound closure of HaCa T keratinocytes via ERK1/2 activation," Mol Cell Biochem (2009) 332:199-205.
Houghton P. et al., "In vitro tests and ethanopharmacological investigations: Wound healing as an example," Journal of Ethanopharmacology 100 (2005) 100-107.
Iftikhar F. et al., "Effects of Acacia Honey on Wound Healing in Various Rat Models," Phytotherapy Research Phytoher: Res 24: 583-586 (2010).
Pieper B. Commentary—"Honey: A Potent Agent for Wound Healing?", J. WOCN 2002, 29, 273-274.
Gethin G. et al., "Case series of use of Manuka honey in leg ulceration," 2005 International Wound Journal, vol. 2, No. 1, pp. 10-15.
Ranzato E. et al., "Signaling Pathways in Wound Repair," In: Wound Healing: Process, Phases and Promoting, 2011, pp. 123-135.
Cipriani V. et al., "Long-term effect of platelet lysate on primary fibroblast highlighted with proteomic approach," Journal of Tissue Engineering and Regenerative Medicine, 2009, 3, pp. 531-538.
Ranzato E. et al., "Scratch wound closure of C2C12 mouse myoblasts is enhanced by human platelet lysate," Cell Biology International 33 (2009) pp. 911-917.
Ranzato E. et al., "Role of ERK 1/2 in Platelet Lysate-Driven Endothelial Cell Repair," Journal of Cellular Biochmistry 100: 783-793 (2010).

(56) References Cited

OTHER PUBLICATIONS

Ranzato E. et al., "Epigallocatechin-3-gallate induces mesothelioma cell death via H2O2—dependent T-type Ca2+channel opening," Journal of Cellular and Molecular Medicine, vol. 16, No. 11, 2012, pp. 2667-2678.

Ranzato E. et al., "Platelet lysate stimulates wound repair of HaCaT keratinocytes," British Journal of Dermatology 2008, 159, pp. 537-545.

Ranzato E. et al., "Hmgb1 Promotes Wound Healing of 3T3 Mouse Fibroblasts via Rage-Dependent ERK1/2 Activation," Cell Biochem Biophys (2010) 57:9-17.

Ranzato E. et al., "High Mobility Group Box Protein-1 in Wound Repair," Cell 2012, 1, pp. 699-710.

Li J. et al., "Platelet derived Growth Factor-stimulated Migration of Murine Fibroblasts is Associated with Epidermal Growth Factor Receptor Expression and Tyrosine Phosphorylation," The Journal of Biological Chemistry, vol. 275, Issue of Jan. 28 2000, pp. 2951-2958.

Wood B et al., "Manuka honey, a low cost leg ulcer dressing," New Zealand Medical Journal, Mar. 28, 1997 (Mar. 28, 1997) p. 107.

Weheida S. et al., "Comparing the effects of two dressing techniques on healing of low grade pressure ulcers," Journal of Medical Research Institute, Alexandria University, 12(2), pp. 259-278 (1991).

Sabacinski K et al., "Necrotizing Fasciitis," The American College of Foot Surgeons, vol. 28, No. 2, 1989, pp. 106-111.

Making Cosmetics, "PVP (polyvinylpyrrolidone)," Fact Sheet, Updated Jun. 27, 2014, pp. 1.

"What Does 'Raw Honey' Really Mean?" Empowered Sustenance, <https://empoweredsustenance.com/raw-honey-definition/>, published Jul. 14, 2014, pp. 1-17.

Zbuchea A., "Up-To-Date Use of Honey for Burns Treatment," Annals of Burns and Fire Disasters, vol. XXVII, No. 1, Mar. 2014.

McLoone et al., "Honey: A Therapeutic Agent for Disorders of the Skin," Central Asian Journal of Global Health, vol. 5, No. 1 (2016).

Andri et al. (Efficacy of Povidone Iodine and Honey Mixture in Laceration Recovery, The Journal of Indonesian Orthopedic, vol. 40, No. 1, Apr. 2012) (Year: 2012).

* cited by examiner

WOUND HEALING COMPOSITIONS COMPRISING BUCKWHEAT HONEY AND METHYLGLYOXAL AND METHODS OF USE

CROSS-REFERENCE TO RELATED APPLICATIONS

This patent application claims the benefit under 35 U.S.C. § 119(e) of U.S. Provisional Patent Application No. 62/109,369, filed Jan. 29, 2015, which application is incorporated herein by reference.

FIELD OF THE INVENTION

The invention broadly relates to a wound healing composition, more specifically to a wound healing composition including a combination of medicinal buckwheat honey and methylglyoxal.

BACKGROUND OF THE INVENTION

Undesirable and dangerous side effects and adverse drug interactions are well known for the predominantly synthetic organic pharmaceuticals that have been widely administered over the past several decades. These adverse effects have led many research groups to go back and study, in greater detail, the medicinal properties and mechanisms of action of many natural compounds. Ancient cultures have long been aware of the medicinal properties of the natural product, honey. The subject matter of the present invention involves novel medicinal activities associated with methylglyoxal-fortified buckwheat honey.

In one embodiment of the present invention, various antibacterial mechanisms are combined into a honey. Previously, different antibacterial mechanisms have been known to exist only separately in honeys derived from different floral sources. Honey has been widely accepted as both food and medicine by most, if not all, generations, traditions, and civilizations, both ancient and modern. Although honey has been used by humans for more than 5,000 years to treat a variety of ailments, it has been recognized for almost as long that honeys derived from some floral sources are more medicinal than others. As a general rule, darker colored honeys have more medicinal activities than light-colored honeys. Many studies have shown that medicinal honey influences biological systems as antioxidant anti-inflammatory, and antimicrobial. In addition honey acts as an autolytic debridement agent on wounds, as a cough suppressant, analgesic, remedy for dyspepsia, and natural anticancer agent.

One of the darkest honeys is buckwheat honey, which has been shown to have one of the highest antioxidant, anti-inflammatory, and antibacterial activities of any honey variety tested. Because of the bacterial resistance problems that have arisen from the overuse and misuse of antibiotics, the antibacterial activity of honey is the activity that has renewed the interest in honey, particularly for treatment of hard-to-heal (chronic) wounds. But the antibacterial activity of honeys derived from different floral sources has been found to be due to different mechanisms. Early on, honey's antibacterial activity was attributed to its osmotic effect and to its low pH, but these have subsequently been found to contribute only minor antibacterial effects. The first factor discovered that contributes a major antibacterial activity in honey was hydrogen peroxide, but it's generation and concentration are under the control of a number of important effects.

First, hydrogen peroxide is not a constituent of the nectar from which honey is produced. It is derived from the enzymatic activity of glucose oxidase acting on glucose. The maturation of honey from plant nectar is dependent upon the activities of several enzymes, most of which are derived from the hypopharyngeal gland of the honey bee. Diastase (amylase), derived from the bee, breaks down starch to smaller carbohydrates (dextrins, oligo-, di- and monosaccharides [glucose]). Invertase, derived from the bee, converts sucrose, the primary sugar in nectar, into glucose and fructose. Glucose oxidase, also derived from the bee, catalyzes the oxidation of glucose by molecular oxygen to gluconolactone, which subsequently hydrolyzes spontaneously to gluconic acid and hydrogen peroxide. Gluconic acid is the primary acid in honey responsible for most of honey's acidity and low pH, and hydrogen peroxide is the primary antibacterial agent in most medicinal honeys.

Second, the production of hydrogen peroxide is very slow in mature honey for two reasons: i) the activity of glucose oxidase is depressed by high osmotic pressure, and ii) the spontaneous conversion of gluconolactone to gluconic acid and hydrogen peroxide is a hydrolysis reaction requiring water, which is unavailable in ripe honey. Most hydrogen peroxide present in ripe honey was generated while water was available as the honey was being ripened and dried by the bees. And when ripened honey is subsequently diluted, by wound fluid for example, this reaction speeds up again. Upon dilution of medicinal honey, the rate of hydrogen peroxide generation is continuous and can reach concentrations in excess of 4 mmol/L, with a mean of about 1-2 mmol/L. This relatively low concentration is nevertheless high enough to provide a substantial antibacterial activity, and yet is about 1000-times less then the 3% solution commonly used as an antiseptic; which high concentration has been associated with tissue damage, including damage to fibroblast cells from human skin. Furthermore, the continuous production of hydrogen peroxide in diluted honey produces a long-lasting antiseptic effect that is most sought after in fighting infections and wounds. It has been reported that hydrogen peroxide is more effective when supplied by continuous generation from glucose oxidase catalysis, as in honey, than when added as a single bolus.

Third, in addition to the glucose/glucose oxidase system as a main source of hydrogen peroxide generation, plant-derived polyphenols present in some honeys provide a supplementary source of hydrogen peroxide. Honeys with high concentrations of polyphenols, such as buckwheat honey, have higher hydrogen peroxide levels due to this second method of hydrogen peroxide generation. The mechanism of this action is likely from the auto-oxidation of polyphenols yielding both hydrogen peroxide and phenoxyl-radicals. Furthermore, redox-active phenolics appear to be active intermediates that confer additional oxidative activity on hydrogen peroxide. In addition, the chemical interaction of honey phenolics with hydrogen peroxide results in products that degrade bacterial DNA. In the presence of transition metal ions, via the Fenton reaction, hydrogen peroxide is also converted to hydroxyl radicals. Both the phenoxyl- and hydroxyl-radicals have been shown to induce strand breaks in DNA. Thus, a second factor present in some honeys that contribute to its antibacterial effect are polyphenols.

A third factor found in honey that has antibacterial activity is methylglyoxal (MGO), but this agent has only been found in honey derived from certain floral species of the *Leptospermum* genus of shrubs and small trees found in New Zealand, Australia, Malaysia, and Indonesia. Originally referred to as UMF (Unique Manuka Factor), methylglyoxal has been found to originate in honey from dihydroxyacetone present in the nectar of *Leptospermum* flowers, for example from the manuka tea tree (*Leptospermum scoparium*) of New Zealand or the jelly bush (*Leptospermum polygalifolium*) of Australia. Since the first description of UMF, it has been recognized that its concentration is highly variable in different manuka honey batches, and that has been determined to be due to different concentrations of dihydroxyacetone in different cultivars of manuka, with pink-flowered cultivars producing the highest dihydroxyacetone levels in nectar. There are also seasonal changes within a *Leptospermum* species, or between the different species. Because of this batch to batch variability, the methylglyoxal levels or antibacterial activity of each lot of *Leptospermum* honey must be assayed to determine whether it will be useful as a medicinal honey or not. As manuka honey often has very low levels of hydrogen peroxide, methylglyoxal becomes its primary antibacterial agent.

A fourth antibacterial factor that has been found in Revamil Source honey that is produced in greenhouses in The Netherlands is Bee Defensin-1, a cationic antimicrobial peptide placed in this honey variety by the bees. Defensins are antimicrobial peptides found in many organisms, including plants, invertebrates, insects, birds and mammals. They are cysteine-rich peptides with multiple disulfide bonds and a triple-stranded beta sheet. Most defensins function by binding to the microbial cell membrane, and once embedded, they form pore-like membrane defects that allow efflux of essential ions and nutrients. Bee Defensin-1, a 51-amino acid peptide (also called Royalisin because it was first discovered in royal jelly), was discovered in Revamil Source honey when bactericidal activity was not eliminated by neutralization of the usual antimicrobial factors (hydrogen peroxide and methylglyoxal). The activity was found in a relatively high molecular weight (>5-kDa) chromatographic fraction; stained as a protein on polyacrylamide gel electrophoresis; and was immuno-stained by anti-bee defensin-1 antibody on a Western blot. In addition, the antibacterial activity of Revamil Source honey was abolished by proteolytic digestion with pepsin and by the anti-bee defensin-1 antibody.

Medicinal honeys from different floral sources exhibit differing antibacterial activities towards different bacterial pathogens. For example, Mundo et al., (2004) reported varying sensitivities to the antibacterial properties of 26 different honey types by nine different bacteria, including multiple strains of *Staphylococcus aureus*, emphasizing the variability in the antibacterial effect of different honey samples. These authors reported that whereas *Bacillus stearothermophilus* was the most sensitive microorganism to the antibacterial activity of medicinal honeys in the study, *Alcaligenes faecalis, Lactobacillus acidophilus*, and *Staphylococcus aureus* strains ATCC 25923, 8095, and 9144 were each moderately sensitive, and *Escherichia coli, Salmonella enterica, Pseudomonas fluorescens, Bacillus cereus*, and *Listeria monocytogenes* were the most resistant to the antibacterial activity of honey.

In the Mundo et al., (2004) study it was demonstrated that different microorganisms had variable susceptibilities to the different antibacterial mechanisms in various honeys. Whereas it required 50% manuka honey with its non-peroxide methylglyoxal antibacterial mechanism to inhibit the growth of *B. stearothermophilus*, buckwheat honey at only 25% concentration was required to inhibit the growth of this organism via its hydrogen peroxide-dependent antibacterial action. The same was true for the inhibition of *S. aureus* strains ATCC 25923 and 9144 which both were inhibited by 50% manuka honey but by only 33% buckwheat honey, whereas the converse was true for the inhibition of *S. aureus* strain ATCC 8095 and *B. cereus* where 50% buckwheat honey was required to completely inhibit their growth while only 25% manuka honey was required. Table 1 summarizes the bacterial sensitivities of the various bacteria to the different honeys.

TABLE 1

Bacterial Sensitivity by Type and Inhibitory Concentration of Honey.

| Bacteria | Type of Honey and (Inhibitory Concentration; % honey in water, w/v) |
|---|---|
| *E. coli* O157:H7 | christmas berry (100); saw palmetto (100); tarweed (100); buckwheat (100); manuka (50) |
| *S. enterica* | manuka (50) |
| *A. faecalis* | blueberry (100); soybean (100); tarweed (33); buckwheat (33); manuka (25); horsemint (25) |
| *P. fluorescens* | tarweed (100); buckwheat (50) |
| *L. acidophilus* | soybean (100); christmas berry (100); buckwheat (100); manuka (100); saw palmetto (100); melaleuca (50); tarweed (50) |
| *L. monocytogenes* | melaleuca (100); tarweed (100); buckwheat (100) |
| *B. cereus* | tarweed (100); buckwheat (50); manuka (25) |
| *S. aureus* ATCC 8095 | christmas berry (100); saw palmetto (50); tarweed (50); buckwheat (50); cotton (33); manuka (25) |
| *S. aureus* ATCC 9144 | saw palmetto (100); sunflower (100); horsemint (100); manuka (50); *melaleuca* (33); buckwheat (33) |
| *S. aureus* ATCC 25923 | soybean (100); sunflower (100); saw palmetto (50); *melaleuca* (50); rabbit bush (50); manuka (50); tarweed (33); buckwheat (33) |
| *B. Steorothermophilus* | blueberry (100); blackberry (100); manuka (50); black sage (50); red sumac (50); *melaleuca* (50); horsemint (50); christmas berry (50); soybean (33); alfalfa (33); cotton (33); saw palmetto (33); rabbit bush (33); tarweed (25); buckwheat (25); knotweed (20); sunflower (17) |

Data from Mundo et al., 2004.

Of the honeys listed in Table 1, buckwheat, tarweed, saw palmetto and *melaleuca* inhibit bacteria primarily via hydrogen peroxide, whereas the antibacterial activity of manuka, blueberry, and knotweed honeys is primarily non-peroxide mediated. Other studies report similar findings and therefore the present disclosure relates to a honey composition containing high concentrations of both peroxide and non-peroxide antibacterial activities in order to produce a honey with broad-spectrum antibacterial activity efficient at inhibiting the growth of most major wound pathogenic bacteria at one low honey concentration.

As can be understood from the wide variety of compositions, devices and methods directed at wound healing, many strategies have been contemplated to accomplish the desired end. Heretofore, widely administered synthetic organic pharmaceuticals are commonly associated with undesirable side effects and adverse drug interactions. Thus, there is a long-felt need for more natural wound healing compositions. There is further a need for wound healing compositions involving medicinal honey and methylglyoxal, and the corresponding methods of use.

BRIEF SUMMARY OF THE INVENTION

The inventive composition of the present disclosure is a medicinal honey with concentrations of hydrogen peroxide, polyphenols and methylglyoxal that are all in the upper concentration range of what are naturally found in various native honeys. This is achieved by fortification of buckwheat honey that is naturally rich in hydrogen peroxide and polyphenols with a stable, medicinal concentration of methylglyoxal. In this composition of the present invention, 'MGO-fortified buckwheat honey' provides a composition containing buckwheat honey with high natural concentrations of hydrogen peroxide and polyphenols to which methylglyoxal is added to a concentration between 500-2000 mg per kg of final honey product. The phrase 'high natural concentrations of hydrogen peroxide and polyphenols' is defined as concentrations that naturally exist in buckwheat honey where the concentration of hydrogen peroxide is in the range of 2-4 mM and where the polyphenol concentration is in the range of 275-575 gallic acid equivalents per gram of honey.

The inventive composition is used in ointment, or wound-dressing formulations to modulate biochemical mechanisms associated with wound healing, including autolytic debridement and the reduction of wound protease activities, active infection and malodor.

These and other objects and advantages of the present invention will be readily appreciable from the following description of preferred embodiments of the invention and from the accompanying examples and claims.

BRIEF DESCRIPTION OF THE DRAWINGS

The nature and mode of operation of the present invention will now be more fully described in the following detailed description of the invention taken with the accompanying figures, in which.

DETAILED DESCRIPTION OF THE INVENTION

Figure 1:
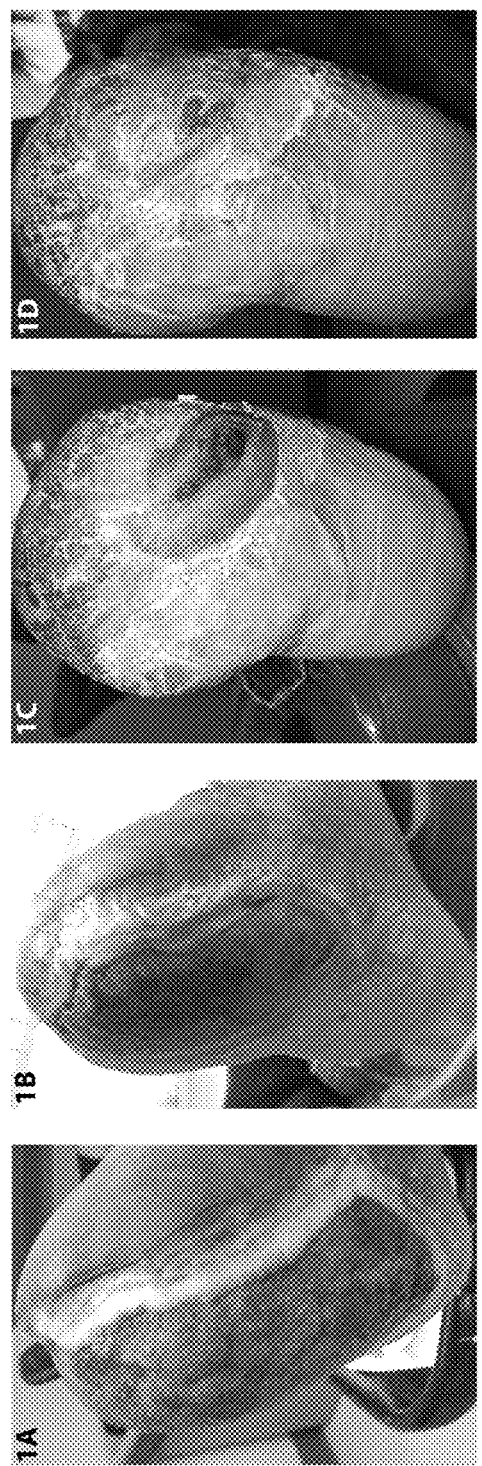
FIG. 1, panels 1A, 1B, 1C, and 1D, shows treatment using the composition of the present invention, MGO-fortified buckwheat honey wound dressings, of a large infected amputation wound in the foot of a diabetic patient.

While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

The present invention provides an exemplary wound healing composition, which includes seasonally harvested raw, strained, monofloral buckwheat honey naturally rich in hydrogen peroxide (containing and/or capable of generating 2-4 mM concentration), polyphenols (275-575 gallic acid equivalents of polyphenol compounds per gram of honey) to which is added the natural antibacterial compound, methylglyoxal to a final concentration of 500-2000 mg per kg of final honey product. This 'MGO-fortified buckwheat honey' has broad-spectrum peroxide and non-peroxide antimicrobial activity effective to reduce the number of viable microorganisms at a wound site.

In another aspect, the present invention provides a wound dressing. The wound dressing is used with the composition and a support. The support includes, but is not limited to, a fibrous gauze material, a hydrogel, a foam, a film, a hydrocolloid, an alginate, a collagen, or a combination of any two or more of the afore-mentioned.

In yet another embodiment, the present invention includes a method of treating a wound. The method includes contacting a wound with any of the above embodiments of the wound dressing.

A "chronic wound," "non-healing wound," slow-to-heal wound," or "stalled wound," as used herein, refers to a wound that fails to heal spontaneously over a 4-12 week timeframe from inception of the wound to complete closure of the skin at the wound site. Such wounds commonly include external dermal wounds.

Skin wounds designated as "chronic" or "non-healing" or "slow-to-heal" or "stalled" are commonly observed in clinical settings as venous leg ulcers, diabetic foot ulcers, pressure ulcers, arterial ulcers, ulcers of mixed etiology, burns, or non-healing surgical wounds. Other types of non-healing wounds are observed in less frequent conditions, such as, fistulae, dermatitis or vasculitis wounds, skin cancers, and radiation burns. This list is not exhaustive and is provided to show examples of such non-healing wounds. Differentiated from "acute" wounds that spontaneously heal without complications in a matter of days or weeks through the four normal phases of the "wound healing curve" (hemostasis, inflammation, proliferation, and remodeling), chronic wounds may persist for months or years and occasionally can last a lifetime, and are therefore commonly referred to as "non-healing" wounds. There is a need for treatment of any of these types of non-healing wounds since spontaneous healing has failed to occur. In chronic wounds, at the cellular biological level, there is commonly a prolonged inflammatory phase often caused by elevated proteases or active infection.

Sometimes prolonged inflammation due to elevated wound proteases and active infection occur simultaneously and prevent wounds of the skin from healing. The present disclosure relates to a composition, and methods for treating wounds of the skin to counteract these pathological conditions. The composition includes a medicinal honey fortified with the additional antimicrobial compound methylglyoxal. The components of the inventive composition surprisingly provide a synergistic effect that results in broad-spectrum peroxide and non-peroxide antibacterial activity that acts to provide suppression of wound protease activities and active infections.

The composition according to the present invention is useful for treating common chronic wounds, such as venous leg ulcers, diabetic foot ulcers, pressure ulcers, arterial ulcers, burns, and non-healing surgical wounds. In addition, the composition according to the present invention is also useful for treating abrasions, lacerations, minor cuts, scalds and burns, and other partial thickness wounds. A useful composition includes, but is not limited to, medicinal honey and methylglyoxal. The composition is advantageously applied in an ointment that is applied to a wound until it is healed (3-8 months) with wound dressing changes every 24-96 hours. Alternatively, the wound healing composition of the present invention is impregnated into or associated with carrier dressing supports (e.g. fibrous gauze, hydrogel, foam, film, hydrocolloid, collagen, or alginate), which are applied to wounds for the times described above.

The present disclosure further provides a method for treating the wound. In some embodiments, the method includes contacting a wound with the composition of the present disclosure wherein the composition includes a medicinal honey fortified with the natural non-peroxide antibacterial compound, methylglyoxal comprising an amount between 500-2000 mg per kg of finished wound healing composition, effective to reduce the number of viable microorganisms at a wound site. The composition is applied to the wound, for example, in an ointment. In some embodiments, the composition is applied to a wound dressing, which is subsequently applied to the wound. Advantageously, a dressing including the composition is contacted with the wound until it is healed (3-8 months) with wound dressing changes every 24-96 hours, thereby providing a moist environment enriched with the MGO-fortified medicinal honey to facilitate healing of the skin or mucosal membrane.

Embodiments

Embodiment 1 is a composition including a medicinal honey with high peroxide-induced and polyphenol-facilitated antimicrobial activity, an effective amount of methylglyoxal (500-2000 mg per kg) to add non-peroxide antimicrobial activity, wherein each of the antimicrobial activities provides a different mechanism of antibacterial inhibition thereby providing a broad-spectrum antimicrobial activity effective to reduce the number of viable microorganisms at a wound site.

Embodiment 2 is the composition of embodiment 1 wherein the medicinal honey is monofloral buckwheat honey that naturally generates 2-4 mM hydrogen peroxide and which naturally contains 275-575 gallic acid equivalents of polyphenol compounds per gram of honey, and wherein the amount of methylglyoxal added is 500-2000 mg per kg of honey.

Embodiment 3 is a wound dressing including the composition of either embodiment 1 or 2; and a support.

Embodiment 4 is a wound dressing of embodiment 3, wherein the support includes a fibrous gauze material, a hydrogel, a foam, a film, a hydrocolloid, an alginate, a collagen, or a combination of any two or more of the afore-mentioned.

Embodiment 5 is a method of treating a wound, including contacting a wound with the composition of either embodiment 1 or 2.

Embodiment 6 is a method of treating a wound, including treating a wound with the wound dressing of either one of embodiments 3 or 4.

Examples

Objects and advantages of this invention are further illustrated by the following examples, but the particular materials and amounts thereof recited in these examples, as well as other conditions and details, should not be construed to unduly limit to this invention.

Example 1 demonstrates the composition of the present invention, embodiments 1 and 2.

Monofloral buckwheat honey fortified with methylglyoxal at a concentration of 1000 mg per kg is prepared and impregnated into acetate non-woven medical grade dressing (approximately 4 g MGO-fortified buckwheat honey in each 4-inch×5-inch dressing), embodiments 3 and 4. The dressings are protected with polyethylene liners applied to both sides, and dressings of 4-inches×5-inches are sealed individually in foil pouches constructed of white polyester film fused to aluminum foil that constitutes an excellent barrier. The dressings are then sterilized with gamma radiation and verified as sterile before use.

Panels 1A, 1B, 1C, and 1D of FIG. 1, show treatment using dressings impregnated with the composition of the present invention, MGO-fortified buckwheat honey, of a large infected open amputation wound in the foot of a diabetic patient, embodiments 5 and 6. A 47 year-old male with a history of plantar diabetic foot ulcers who had recently had all the toes on his left foot amputated and the dermal layer on a significant portion of the underside of his foot excised to remove infected tissue (Panel 1A) presented with extensive infection in the open wound on the plantar aspect of his foot. After sharp debridement of this severely infected open amputation wound to remove slough, eschar, and necrotic tissue, the manufactured sterile MGO-fortified buckwheat honey dressings were cut to closely fit the wound size using sterile scissors and applied to the wound, with dressing changes every two days (48 hours). On day 0, the wound measured 12 cm×8 cm (Panel 1A: wound area 96 $cm^2$). The patient was instructed on how to change his own dressings every 48 hours. After three weeks of treatment with the sterile MGO-fortified buckwheat honey dressings, the wound area decreased 7.8-fold to 12.25 $cm^2$ (Panel 1B), a wound area reduction of 87%. Many wound healing trajectory studies in the literature indicate that a wound area reduction of greater than 50% within 4 weeks of treatment indicates that full wound closure will occur within 12-20 weeks of continued treatment. This wound was no exception to that expectation, fully closing after 12 weeks of treatment with the MGO-fortified buckwheat honey dressings, having a wound area of 2.6 $cm^2$ after 8 weeks of treatment (Panel 1C), and less than 0.4 $cm^2$ after 11 weeks of treatment (Panel 1D).

Example 2 demonstrates the composition of the present invention, embodiments 1 and 2.

Figure 2:
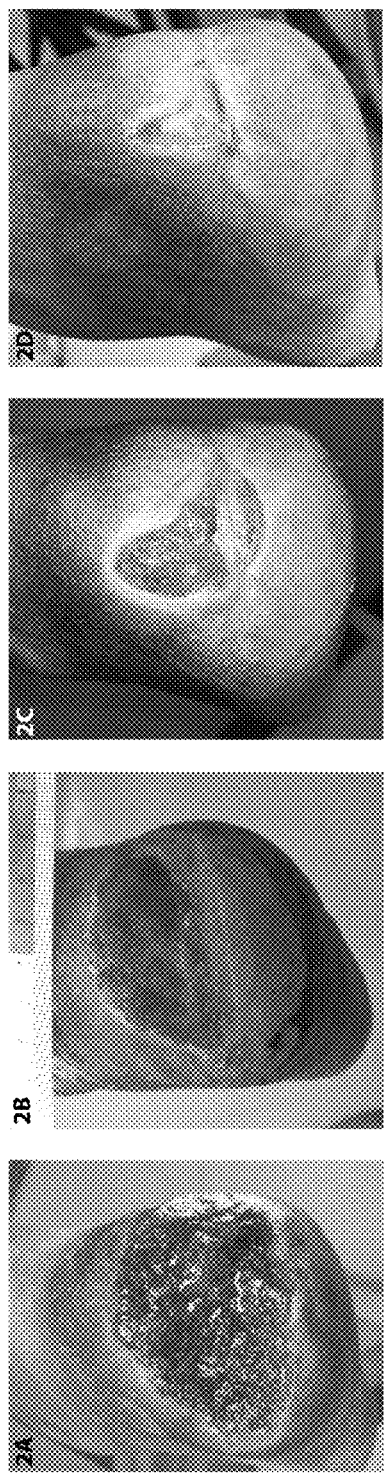
FIG. 2, panels 2A, 2B, 2C, and 2D, shows treatment using the composition of the present invention, MGO-fortified buckwheat honey wound dressings, of a large deep pressure ulcer.
Figure 3:
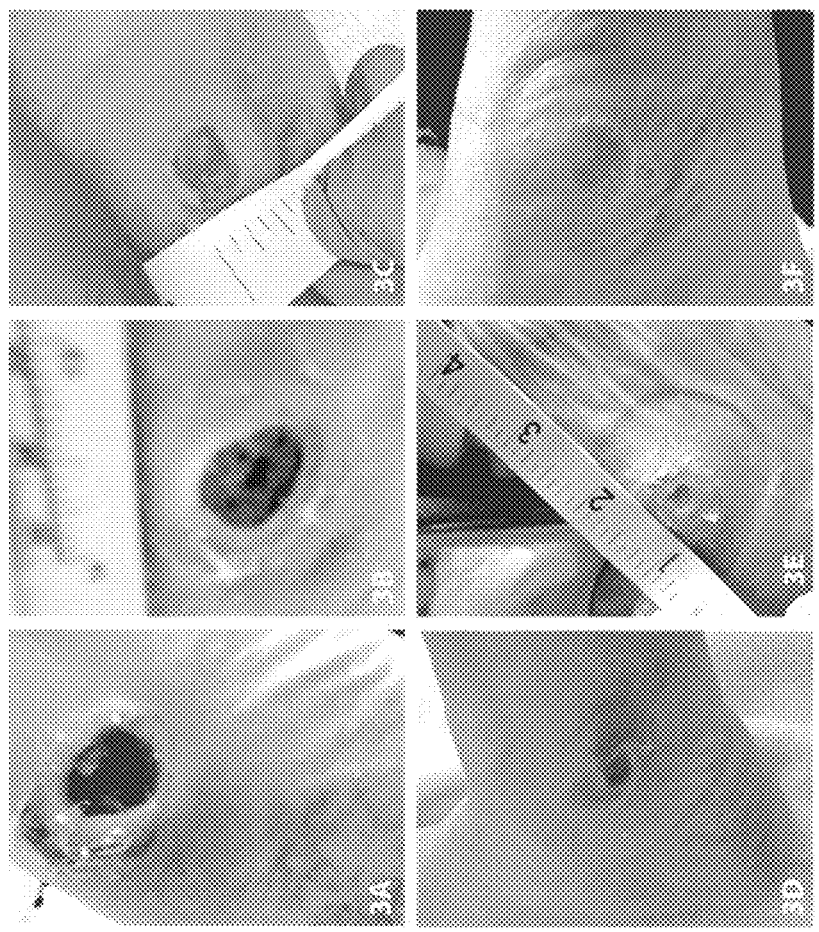
Figure 4:
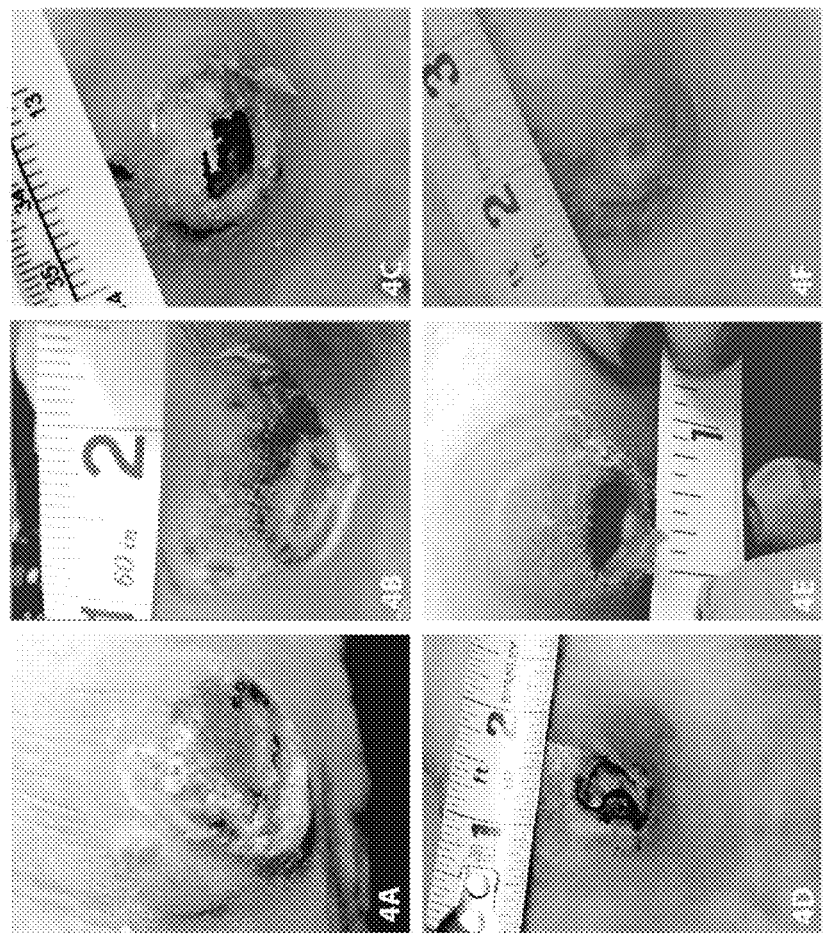

Panels 2A, 2B, 2C, and 2D, depicted in FIG. 2, show treatment using dressings impregnated with the composition of the present invention, MGO-fortified buckwheat honey, of a large deep pressure ulcer. The MGO-fortified buckwheat honey dressings were used to treat this pressure ulcer situated on the right heel of a 59 year-old male. This patient has a history of diabetes and immobility. Before onset of treatment with the sterile MGO-fortified buckwheat honey dressings, the wound measured approximately 6.3 cm×4.4 cm (Panel 2A: 27.7 $cm^2$). The patient was instructed on how to change his own dressings every 48 hours. After three weeks of treatment with the sterile MGO-fortified buckwheat honey dressings, the wound area had decreased to 11.2 $cm^2$ (Panel 2B), a 60% reduction in the wound area, and again greater than the 50% wound area reduction within 4 weeks of treatment that is indicative of complete closure within a 12-20 week time frame. This large pressure ulcer had reduced in wound area to 4.4 $cm^2$ after 9 weeks of treatment (Panel 2C), and as expected, went on to completely close after 13 weeks of treatment with the sterile MGO-fortified buckwheat honey wound dressings (panel 2D).

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

The invention claimed is:

1. A wound healing composition consisting essentially of:
   buckwheat honey; and
   methylglyoxal in an amount of from about 500 to about 2000 mg per kg of the total composition.

2. A wound healing dressing comprising:
   the wound healing composition according to claim 1; and
   a support.

3. The wound healing dressing of claim 2, wherein the support is selected from the group consisting of a fibrous gauze material, a hydrogel, a foam, a film, a hydrocolloid, a collagen, an alginate, and a combination of two or more thereof.

4. The wound healing dressing of claim 2, wherein the wound healing dressing is capable of being replaced on a wound at least once.

\* \* \* \* \*